(12) United States Patent
Rosengrant

(10) Patent No.: US 6,402,727 B1
(45) Date of Patent: Jun. 11, 2002

(54) DISPOSAL COVER FOR USED FEMININE PROTECTION PRODUCTS

(76) Inventor: Georgene Elaine Rosengrant, P.O. Box 73, Caledonia, NY (US) 14423

( * ) Notice: Subject to any disclaimer, the term of this patent is extended or adjusted under 35 U.S.C. 154(b) by 0 days.

(21) Appl. No.: 09/489,814

(22) Filed: Jan. 24, 2000

(51) Int. Cl.[7] .............................. A61F 13/15; A61F 13/20
(52) U.S. Cl. ............................ 604/385.02; 604/385.13; 206/440
(58) Field of Search ................... 604/385.02, 385.06, 604/385.13, 385.19, 390; 206/440; 53/416, 461, 135.2; 128/830

(56) References Cited

U.S. PATENT DOCUMENTS 3,392,503 A  *  7/1968  Vaughan ...................... 53/461
3,973,567 A  *  8/1976  Srinivasan et al. .... 604/385.05
5,399,177 A  *  3/1995  Blaney et al. .............. 604/389

* cited by examiner

*Primary Examiner*—John G. Weiss
*Assistant Examiner*—Michele Kidwell

(57) ABSTRACT

A disposal cover comprising a single sheet of flexible material with a tape fastening system applied to the sheet's perimeters is disclosed. In the preferred embodiment, the sheet has two outwardly curved sides which taper toward two opposing ends. In use, a used sanitary item, either a pad or a tampon, is placed longitudinally in the center of the cover, and the curved sides and tapered ends are folded until they overlap, and then are fastened together with a tape fastening system. This results in the used sanitary item being completely concealed in a compact, sanitary package that can be easily and discreetly disposed of through the solid waste system.

2 Claims, 2 Drawing Sheets

DISPOSAL COVER FOR USED FEMININE PROTECTION PRODUCTS

BACKGROUND—FIELD OF INVENTION

This invention relates to sanitary disposal mechanisms, specifically to an improved disposal method for used sanitary napkins and tampons.

BACKGROUND—PRIOR ART

Proper disposal of used individual sanitary napkins and tampons is important for sanitary and discretionary purposes. Currently, there is little available to facilitate disposal of such items. Attempts have been made through various inventions to remedy this problem of proper disposal. However, these inventions have not covered all of the disposal needs relating to used feminine protection products.

Inventions have been created where the disposable wrapper for a sanitary pad is an inherent part of the pad. U.S. Pat. No. 4,692,162 to Binker and Miranda (1987) and U.S. patent 4,581,027 to Alvarado (1986) both deploy such a method as does U.S. Pat. No. 3,035,578 to Elmore (1962). There are a number of disadvantages in approaching disposal in this way. These inventions can only be used with sanitary napkins, not with tampons. Also, the disposable wrapper, being attached to the underside of the pad while the pad is being worn, has a possibility of becoming covered with menstrual fluid from an overused or improperly placed pad, thus causing an unsanitary disposable wrapper. Also, the wrapper cannot be produced as a separate product. These wrappers add another layer of material to the pad, making the pad bulkier and more uncomfortable.

U.S. Pat. No. 5,740,554 to Reed (1998) addresses this disposal problem with a mitten device which is used to remove the tampon, then folds over the used tampon, making it ready for disposal. This device is awkward and time consuming to use. Also, there is a possibility of tearing, while the mitten is being pulled onto the user's hand, thus creating holes in the disposable cover which would lead to leakage of menstrual fluid through the holes. This device can only be used with tampons. Also, this product would be more expensive and more difficult to manufacture due to the various sections. (The device has four different portions an index finger, a thumb, a mid-section, and a cuff portion.) The mitten shape could cause the sides to collapse together, making it difficult and time consuming to open prior to inserting the used tampon.

U.S. Pat. No. 5,193,684 to McDonald (1993) discloses an invention for a Tampon Disposal Unit. Here, an opening in a folded bag is placed over a cavity, and as the tampon is withdrawn from the cavity into the bag, the bag unfolds longitudinally, then is sealed at the opening. This device exhibits many problems. Only tampons can be disposed of with this appliance. All of its various parts lend to a more expensive, more difficult manufacturing process. The complicated design and various parts would cause confusion as to the proper use of the device. The various steps needed to use this device, including proper placement of the device over the cavity, threading the tampon string through the hole in the bottom of the bag, pulling the tampon into the bag without misplacement, all contribute to the difficulty of using this device. Also, preventing leakage of menstrual fluid around the outside of the bag while withdrawing the tampon from the cavity would be very difficult.

Another attempt to aid the sanitary disposal of used feminine protection products has been through inventions for disposable waste bags. U.S. Pat. No. 4,996,727 to Wyatt (1991) exhibits a bag which is comprised of three layers of material and a handle. Aside from being expensive and difficult to manufacture, this device would be clumsy to use. This device would require the user to fit the used item into the bag, which could also result in messy residue around the opening. U.S. Pat. No. 4,765,477 to Froidh et al. (1988) discloses a wrapper for the clean sanitary article, which, after removed, can be used as a disposal bag for the used sanitary article. U.S. Pat. No. 5,484,636 to Berg, Jr., et al. (1996) has a similar system with a pouch on the sanitary napkin wrapper which can be used for disposal of the used sanitary napkin after the clean pad is removed from the wrapper. Users typically remove and discard the soiled article prior to opening and inserting a clean article. The user would have to remove the clean article to render the wrapper usable as a disposal device. The clean sanitary article would have to be laid on a contaminated surface (sink, top of toilet, etc.) while disposing of the used article. Preparing the bag for disposal, removing the soiled article, wrapping it for disposal, and inserting the clean article, would be impossible without laying either the clean or soiled article down on a surface. Laying a soiled article down would contaminate the surface with bloody menstrual fluid. This creates a very awkward situation for the user and decreases the probability that the disposal bag would be used.

The plumbing system has also been a means for disposal of used tampons. Some users will flush their tampons down the toilet. However, this can not be done with other solid waste in the toilet. And, the low water toilets, which are the new standard, do clog with just a used tampon being flushed through the system. Sanitary pads cannot be disposed of in this way.

SUMMARY OF THE INVENTION

The present invention of a disposal cover for used feminine protection items, comprised of a flat piece of flexible material with a tape fastening system for securing perimeters of the material together, exhibits the following objects and advantages. This invention provides a disposal cover for used feminine protection products, with an optional scent to mask odors, which will allow the used tampon or sanitary pad to be disposed of in a discreet and sanitary manner. This cover furnishes a means of disposal which is easy and convenient to use, and takes little time to manipulate. This invention provides a disposal cover which is easy to prepare for use, and would afford the user a minimal number of steps to dispose of the used sanitary item. This disposal device can be temporarily attached to the outside of the sanitary device wrapper or as a completely separate product apart from the sanitary device. This device provides a disposal mechanism which can be used for both pads and tampons. It would be simple and inexpensive to manufacture, thus creating an inexpensive disposal item. This disposal cover will not become soiled on the outer (or second) surface of the cover since the used sanitary item only comes into contact with the inner (or first) surface. Since sanitary napkins become bulky after they absorb moisture, making the sanitary napkin compact by use of this cover would facilitate convenient, discreet, and efficient disposal of the sanitary napkin.

Further objects and advantages are to provide a discreet, efficient means of disposal for the used feminine protection item, so it will be more readily disposed of through the solid waste system as opposed to the plumbing system (which can become clogged). Also, during times of electrical power outage or water shortage, whether from emergency or other causes, the flushing of toilets would be limited. The invention presented here would provide a hygienic means of disposal, obviating the need for flushing the used sanitary item down the toilet.

Still further objects and advantages will become apparent from a consideration of the ensuing description and drawings.

DRAWING FIGURES

DESCRIPTION OF THE PREFERRED EMBODIMENTS

Figure 1:
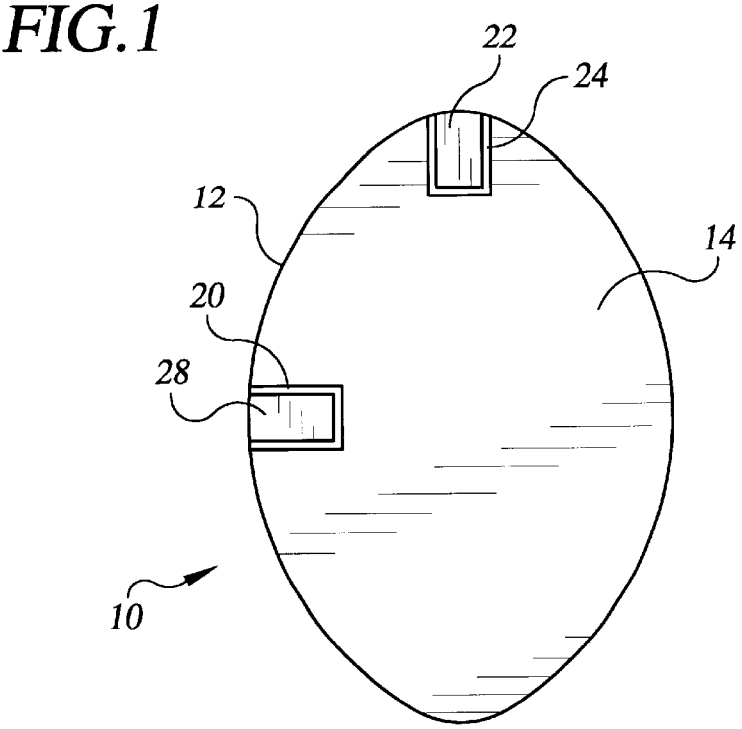
FIG. 1 is a plan view of the first surface of a disposal cover with the second portions of the adhesive tapes positioned on release-treated landing surfaces on the top and side of the cover.
Figure 2:
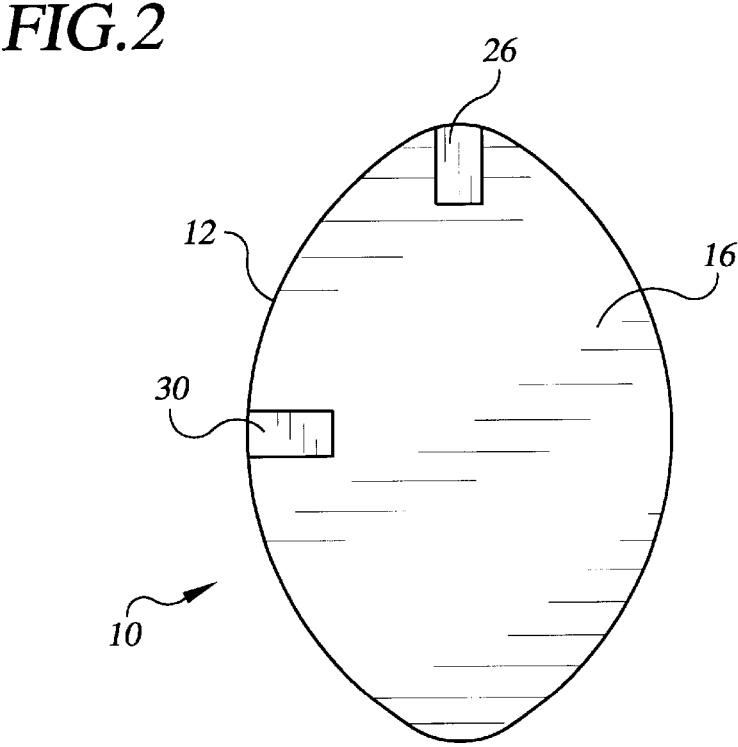
FIG. 2 is a plan view of the second surface of a disposal cover with the first portions of the adhesive tapes positioned on the top and side of the cover.

Referring to FIGS. 1 and 2, the disposal cover 10 includes a single, flexible plastic sheet 12 having a first surface 14 and a second surface 16. The sheet can be of any flexible material such as rubber, polyethylene, or the like. The sheet 12 having a width and a length respectively greater than the width and the length of the used sanitary item which is being disposed.

On the first surface 14 of the sheet (FIG. 1) at the top is the second portion of a rectangular shaped tape 22 which can be of any flexible paper or plastic material. The underside of the tape, which faces the first surface of the sheet when folded downward, is coated with a sticky adhesive. The tape is folded down onto a complementary release-treated landing member 24. The landing member 24, which may be comprised of wax or silicone coated paper or the like, has the underside permanently affixed to the first surface 14 of the sheet with hot melt glue or some other similar substance. The wax or silicone or other similar means of coating on the landing member allows the adhesive tape to be easily separated from the landing member's surface. The complementary landing member 24 is slightly larger than the adhesive tape 22 so as to form a border of release treated material around the adhesive tape 22 when the adhesive tape is folded down onto the landing member. This facilitates the release of the adhesive tape 22 from the landing member 24. The adhesive on the underside of the tape 22 temporarily attaches the tape to the landing member.

On the curved side of the sheet on the first surface 14 (FIG. 1) is the second portion of a rectangular shaped tape 28, which may be comprised of a flexible paper or plastic material with a coating of adhesive material on the underside of the tape. The underside of the tape faces the first surface of the sheet when folded downward. The adhesive tape 28 is folded down onto a complementary release-treated landing member 20. The landing member 20, which may be comprised of a wax or silicone treated paper or the like, has the underside permanently affixed to the first surface of the sheet with hot melt glue or some other similar substance. The wax or silicone or other similar means of coating on the landing member allows the adhesive tape to be easily separated from the landing member's surface. The adhesive on the underside of the tape 28 temporarily attaches the tape to the landing member. The landing member 20 is slightly larger than the adhesive tape 28 which creates a border of release treated material around the adhesive tape 28 when the adhesive tape is folded down and positioned onto the landing member 20. This enables a user to pull the adhesive tape away from the landing member more easily.

On the second surface 16 of the sheet 12 (FIG. 2) at the top tapered end is the first portion of a rectangular shaped tape 26 which rests on the second surface of the sheet. The paper or plastic material comprising the first portion of the adhesive tape 26 is an elongated rectangle which extends above the top tapered end of the second surface of the sheet to become the second portion of the adhesive tape 22. The second portion of the adhesive tape 22 is folded over the top tapered end and folded downward, with the underside of the tape resting against the contemporary landing member 24. The underside of the first portion of the tape 26 is permanently affixed with hot melt glue to the second surface 16 of the sheet of the cover. This first portion of the tape 26 anchors the second portion of the adhesive tape 22 onto the disposal cover so that when the second portion of the adhesive tape 22 is pulled away from the landing member 24, the adhesive tape cannot be pulled off the sheet of the cover.

On the curved side of the sheet on the second surface 16 is the first portion of a rectangular shaped tape 30 with the underside permanently affixed with hot melt glue or the like to the second surface 16 of the sheet of the cover. The paper or plastic material comprising the first portion of the adhesive tape 30 is an elongated rectangle which extends beyond the edge of the curved side of the second surface of the sheet and becomes the second portion of the adhesive tape 28. The second portion of the adhesive tape is folded over the curved side and folded downward, with the underside of the tape resting against the contemporary landing member 20. This first portion of the adhesive tape 30 anchors the second portion of the adhesive tape 28 onto the disposal cover so that when the second portion of the adhesive tape 28 is pulled away from the landing member 20, the adhesive tape cannot be pulled off the sheet of the cover.

A number of advantages of my disposal cover become apparent from the above description:

(a) Used feminine protection products can be completely concealed in a cover which will not leak menses fluid, thus allowing the used feminine protection item to be disposed of in a discreet and sanitary manner.

(b) A minimal number of steps are required to conceal the used tampon or napkin, which contributes to the ease and efficiency of use.

(c) Due to the nature of this disposal cover, it can be temporarily attached to the outside of the wrapper of an unused feminine protection product or function as a separate product apart from the feminine protection product.

(d) Exemplary sanitary items for disposing in this cover include tampons and sanitary napkins.

(e) The second surface comprising the outer side of this cover will not become soiled with menses because it is not attached to a pad in use and because the second surface of the disposal cover does not come into contact with the used item.

(f) The user will be less likely to use the plumbing system for disposal (which can be detrimental to the plumbing system) when provided with a quick, easy, and discreet means of disposing pads and tampons through the solid waste system.

Referring to FIGS. 3–6, using this cover to conceal used feminine protection items is accomplished in, but not limited to, a series of sequential steps.

Figure 3:
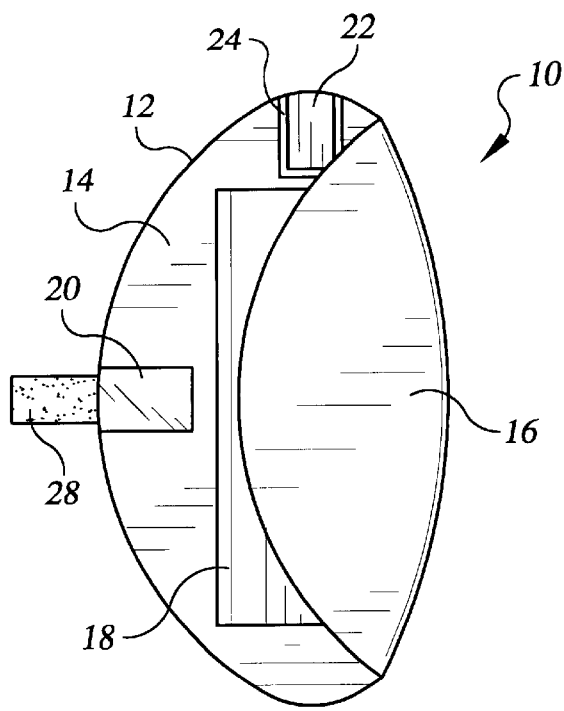
FIG. 3 is a plan view of a disposal cover with a first curved side folded over a used napkin.

To conceal a used feminine napkin, one begins the process as shown in FIG. 3 by doing the following: one lays the napkin 18 in the center of the first surface 14 of the sheet 12 along the longitudinal axis of the cover with each end of the feminine napkin adjacent to the tapered ends of the cover. Then the user folds the first curved side (the side without the adhesive tape) of the sheet over the napkin so the edge of this first curved side of the cover lies in a parallel fashion above the longitudinal axis of the center of the napkin. The adhesive tape 28 on the complementary landing member 20, which is affixed to the first surface of the sheet on the second curved side, is pulled up, away from the landing member so as to expose the sticky underside of the adhesive tape.

Figure 4:
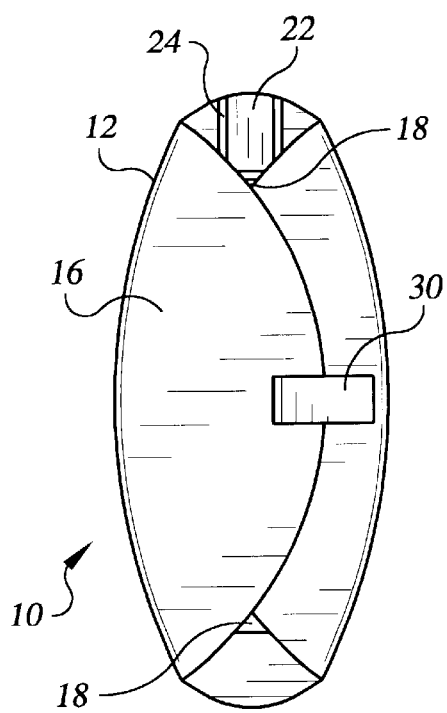
FIG. 4 is a plan view of the disposal cover of FIG. 3 with a second curved side opposite the first curved side folded over against and overlapping the first side, the second side secured to the first side with an opened adhesive tape.

The second step of the process of using this disposal cover is illustrated in FIG. 4. The mechanism of operation is described as follows. The second curved side of the sheet opposite the first curved side is folded over the exposed side of the feminine napkin and against and overlapping the first curved side so as to cover the exposed surface of the used napkin along its longitudinal axis. After the second curved side of the sheet overlaps the first curved side, the sticky surface on the underside of the opened adhesive tab 30 is pressed against the second surface of the sheet on the vicinity of the first curved side to secure the tape against the second surface of the sheet.

Figure 5:
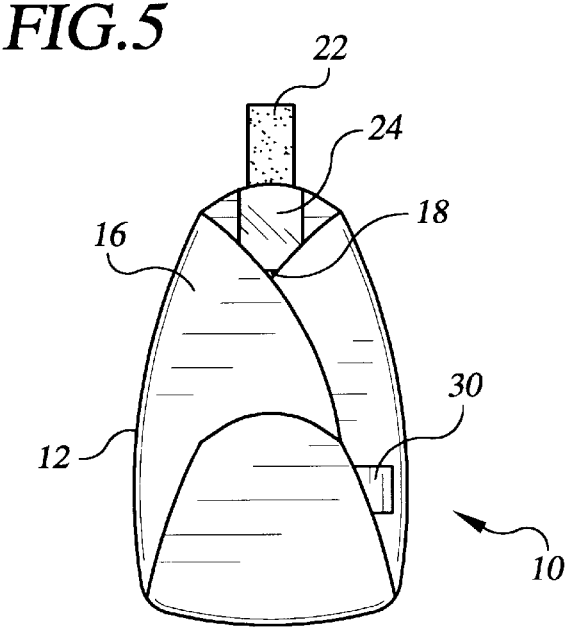
FIG. 5 is a plan view of the disposal cover of FIG. 4 with the bottom tapered end of the cover folded up and over the end of the used feminine napkin.

The third step of the process is shown in FIG. 5, and the procedures involved in this third step are described as follows. The bottom tapered end of the cover, opposite to the top tapered end which contains the adhesive tape 22, is folded upward so that the bottom tapered end lands in the approximate center of the sheet of the cover, and the adhesive tape 22 is pulled upward, away from the landing member 24, so as to expose the sticky surface on the underside of the adhesive tape.

Figure 6:
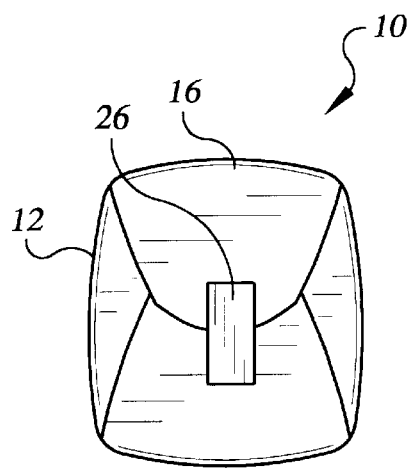
FIG. 6 is a plan view of the disposal cover of FIG. 5 with the top tapered end folded down and secured to the bottom tapered end with an opened adhesive tape so that the feminine napkin is completely concealed.

The final step in using this disposal cover, as shown in FIG. 6, involves the following procedures. The top tapered end containing the opened adhesive tape is folded downward toward the approximate center of the sheet of the cover until the top tapered end overlaps the bottom tapered end (which is in a folded-up position), upon which the sticky underside of the opened adhesive tape 26 is pressed against the second surface of the sheet at the bottom tapered end of the cover. Pressing this sticky surface which is on the underside of the opened adhesive tape against the second surface 16 of the sheet secures the adhesive tape against the second surface of the sheet. The used feminine napkin is now completely concealed in a cover which is neat and compact. This discreet, sanitary package can be tossed into a garbage can or other solid waste disposal receptacle.

CONCLUSION, RAMIFICATIONS, and SCOPE

Accordingly, the reader can see that this invention of a sanitary cover can be used quickly and efficiently to enclose a used feminine protection device inside a barrier which will allow for discreet, hygienic disposal of the item in the solid waste system.

Although the description of the invention in this application contains many specificities, these should not be construed as limiting the scope of the invention but as merely providing illustrations of some of the presently preferred embodiments of this invention. A plurality of modifications are conceivable within the use of the patent claims. For example, the disposal cover can be sealed in a number of ways. The disposal cover can have a variety of shapes, such as circular, oval, rectangular, etc. The disposal cover can be made of various liquid-impervious materials such as plastic, rubber, or the like. The disposal cover can have a range of sizes and thicknesses, which can be customized to what is required to properly accommodate the used sanitary item, whether it be a pad or a tampon.

Thus the scope of the invention should be determined by the appended claims and their legal equivalents, rather then by the examples given.

What is claimed is:

1. A feminine sanitary item disposal cover comprising a single sheet having a first surface and a second surface, said sheet having a width and a length respectively greater than a width and a length of a used feminine sanitary item, said sheet having a tape fastening system for securing a perimeter of said sheet to said second surface, said tape fastening system comprising:

(a) a tape having a first portion and a second portion, a first inner surface facing toward said second surface of said sheet and a second inner surface facing toward said first surface of said sheet, and (b) said first portion comprising a first adhesive disposed on said first inner surface for permanently affixing said first inner surface to said second surface of said sheet, and (c) said second portion of said tape extending beyond edge of said second surface of said sheet, said second portion comprising a second adhesive disposed on said second inner surface for temporarily affixing said second inner surface to a complementary landing member, said complementary landing member comprising:

(d) a tab having an inner surface comprising a third adhesive that may be permanently affixed to said first surface of said sheet, and an outer releasable surface to which said second inner surface of said second portion of said tape is releasably affixed, and (e) said second adhesive on said second portion of said tape would be sufficiently strong to be permanently affixed to said second surface of said sheet after said second portion is manually released from said releasable surface of said complementary landing member, and wherein said tape fastening system may be located on a top tapered end of said sheet and on an outwardly curved side of said sheet to secure two perimeters of said sheet to said second surface of said sheet, whereby said tape fastening system permanently bonds said two perimeters of said sheet to said second surface of said sheet.

2. The disposal cover of claim 1 wherein said complementary landing member being of such a size and shape that said outer releasable surface will form a border of releasable material around said second portion of said tape when said second portion is temporarily affixed to said complementary landing member.

* * * * *